(12) United States Patent
Enmark et al.

(10) Patent No.: US 6,277,976 B1
(45) Date of Patent: *Aug. 21, 2001

(54) OR-1, AN ORPHAN RECEPTOR BELONGING TO THE NUCLEAR RECEPTOR FAMILY

(75) Inventors: Eva L. K. Enmark, Tullinge; Jan-Ake Gustafsson, Stockholm, both of (SE)

(73) Assignee: Karo Bio AB, Huddinge (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/776,844
(22) PCT Filed: Aug. 16, 1995
(86) PCT No.: PCT/EP95/03247
§ 371 Date: Jun. 24, 1997
§ 102(e) Date: Jun. 24, 1997
(87) PCT Pub. No.: WO96/05300
PCT Pub. Date: Feb. 22, 1996

(30) Foreign Application Priority Data

Aug. 16, 1994 (GB) .................................. 9416536

(51) Int. Cl.[7] .................................. C12N 15/12
(52) U.S. Cl. .................. 536/23.5; 435/69.1; 435/252.3; 435/320.1
(58) Field of Search ..................... 530/350; 435/69.1; 536/23.5

(56) References Cited

U.S. PATENT DOCUMENTS 5,639,616 * 6/1997 Liao et al. ............................ 435/7.1

FOREIGN PATENT DOCUMENTS

9306215 * 4/1993 (WO) .

OTHER PUBLICATIONS

George et al., Macromolecular Sequencing and Synthesis, Selected Methods and applications, 127–149, 1988, Alan R. Liss, Inc., 1988.*
Ayala et al., Modern Genetics, 45–48, 1980, Benjamin/Cummings Publishing Company Inc., Menlo Park, California.*

* cited by examiner

Primary Examiner—John Ulm
(74) Attorney, Agent, or Firm—Todd E. Garabedian (57) ABSTRACT

This invention provides an isolated receptor having the amino acid sequence of FIG. 1 (SEQ ID NO:2) or substantially the same amino acid sequence as the amino acid sequence shown in FIG. 1 (SEQ ID NO:2) or an amino acid sequence functionally similar to that sequence, and DNA sequences encoding such a receptor.

7 Claims, 8 Drawing Sheets

```
  1    MSSPTSSLDT  PLPGNGSPQP  STSSTSPTIK  EEGQETDPPP  GSEGSSSAYI

51    VVILEPEDEP  ERKRKKGPAP  KMLGHELCRV  CGDKASGFHY  NVLSCEGCKG

101    FFRRSVVHGG  AGRYACRGSG  TCQMDAFMRR  KCQLCRLRKC  KEAGMREQCV

151    LSEEQIRKKK  IQKQQQQPP   PPTEPASGSS  ARPAASPGTS  EASSQGSGEG

201    EGIQLTAAQE  LMIQQLVAAQ  LQCNKRSFSD  QPKVTPWPLG  ADPQSRDARQ

251    QRFAHFTELA  IISVQEIVDF  AKQVPGFLQL  GREDQIALLK  ASTIEIMLLE

301    TARRYNHETE  CITFLKDFTY  SKDDFHRAGL  QVEFINPIFE  FSRAMRRLGL

351    DDAEYALLIA  INIFSADRPN  VQEPSRVEAL  QQPYVEALLS  YTRIKRPQDQ

401    LRFPRMLMKL  VSLRTLSSVH  SEQVFALRLQ  DKKLPPLLSE  IWDVHE*
```

| | | | | | |
|---|---|---|---|---|---|
| 1 | MSSPTSSLDT | PLPGNGSPQP | STSSTSPTIK | EEGQETDPPP | GSEGSSSAYI |
| 51 | VVILEPEDEP | ERKRKKGPAP | KMLGHELCRV | CGDKASGFHY | NVLSCEGCKG |
| 101 | FFRRSVVHGG | AGRYACRGSG | TCQMDAFMRR | KCQLCRLRKC | KEAGMREQCV |
| 151 | LSEEQIRKKK | IQKQQQQQPP | PPTEPASGSS | ARPAASPGTS | EASSQGSGEG |
| 201 | EGIQLTAAQE | LMIQQLVAAQ | LQCNKRSFSD | QPKVTPWPLG | ADPQSRDARQ |
| 251 | QRFAHFTELA | IISVQEIVDF | AKQVPGFLQL | GREDQIALLK | ASTIEIMLLE |
| 301 | TARRYNHETE | CITFLKDFTY | SKDDFHRAGL | QVEFINPIFE | FSRAMRRLGL |
| 351 | DDAEYALLIA | INIFSADRPN | VQEPSRVEAL | QQPYVEALLS | YTRIKRPQDQ |
| 401 | LRFPRMLMKL | VSLRTLSSVH | SEQVFALRLQ | DKKLPPLLSE | IWDVHE* |

*FIG. 1*

```
   1  CAAGTGCTGT GGAGGAGCAA TCACCGGTGC GGACACAGAG CTCCCGCCTC
  51  CCACAGCCAT TTCCAGGGTA ACGAAGTAGG AGACCCCCTC CTGCGACCCC
 101  CTCACGATCG CCGGTGCAGT CATGAGCCCC GCCTCCCCCT GGTGCACGGA
 151  GAGGGGCGGG GCCTGGAACG AGGCTGCTTC GTGACCCACT ATGTCTTCCC
 201  CCACAAGTTC TCTGGACACT CCCTTGCCTG GAATGGTTC TCCCCAGCCC
 251  AGTACCTCCT CCACTTCACC CACTATTAAG GAGGAGGGAC AGGAGACTGA
 301  TCCACCTCCA GGCTCTGAAG GGTCCAGCTC TGCCTACATC GTGGTCATCT
 351  TAGAGCCAGA GGATGAACCT GAGCGCAAGC GGAAGAAGGG TCCGGCCCCG
 401  AAGATGCTGG GCCATGAGCT GTGCCGCGTG TGCGGGGACA AGGCCTCGGG
 451  CTTCCACTAC AATGTGCTCA GTTGTGAAGG CTGCAAAGGC TTCTTCCGGC
 501  GTAGCGTGGT CCATGGTGGG GCCGGGCGCT ATGCCTGTCG GGGCAGCGGA
 551  ACCTGCCAGA TGGATGCCTT CATGCGGCGC AAGTGCCAGC TCTGCAGACT
 601  GCGCAAGTGC AAGGAGGCTG GCATGCGGGA GCAGTGCGTG CTTTCTGAGG
 651  AGCAGATTCG GAAGAAAAAG ATTCAGAAGC AGCAACAGCA GCAGCCACCG
 701  CCCCCGACTG AGCCAGCATC CGGTAGCTCA GCCCGGCCTG CAGCCTCCCC
 751  TGGCACTTCG GAAGCAAGTA GCCAGGGCTC CGGGGAAGGA GAGGGCATCC
 801  AGCTGACAGC GGCTCAGGAG CTGATGATCC AACAGTTAGT TGCCGCGCAG
 851  CTGCAGTGCA ACAAGCGATC TTTCTCCGAC CAGCCTAAAG TCACGCCCTG
 901  GCCCTTGGGT GCAGACCCTC AGTCCCGAGA CGCTCGTCAG CAACGCTTTG
 951  CCCACTTCAC TGAGCTAGCC ATCATCTCAG TCCAGGAGAT CGTGGACTTC
1001  GCCAAGCAGG TGCCAGGGTT CCTGCAGCTG GGCCGGGAGG ACCAGATCGC
1051  CCTCCTGAAG GCATCCACCA TCGAGATCAT GTTGCTAGAG ACAGCCAGAC
1101  GCTACAACCA CGAGACAGAG TGCATCACGT TCCTGAAGGA CTTCACCTAC
```

*FIG. 2A*

```
1151  AGCAAGGACG ACTTCCACCG TGCAGGCTTG CAGGTGGAGT TCATCAATCC
1201  CATCTTTGAG TTCTCTCGGG CTATGCGTCG GCTGGGCCTA GACGATGCAG
1251  AGTATGCCTT GCTCATTGCC ATCAACATCT TCTCAGCGGA CCGGCCTAAT
1301  GTGCAGGAGC CCAGCCGTGT GGAGGCTCTG CAGCAGCCCT ATGTGGAGGC
1351  CCTCCTCTCC TACACGAGGA TCAAGCGGCC GCAGGACCAG CTGCGCTTCC
1401  CACGAATGCT CATGAAGCTG GTGAGCCTGC GCACCCTCAG CTCCGTGCAC
1451  TCGGAGCAGG TTTTCGCATT GCGTCTCCAG GACAAGAAGC TGCCGCCTTT
1501  GCTGTCCGAG ATCTGGGATG TGCATGAGTA GGGGCCGCCA CAAGTGCCCC
1551  AGCCTTGGTG GTGTCTACTT GCAGATGGAC GCTTCCTTTG CCTTTCCTGG
1601  GGTGGGAGGA CACTGTCACA GCCCAGTCCC CTGGGCTCGG GCTGAGCGAG
1651  TGGCAGTTGG CACTAGAAGG TCCCACCCCA CCCGCTGAGT CTTCCAGGAG
1701  TGGTGAGGGT CACAGGCCCT AGCCTCTGAT CTTTACCAGC TGCCCTTCCT
1751  CCCGAGCTTA CACCTCAGCC TACCACACCA TGCACCTTGA GTGGAGAGAG
1801  GTTAGGGCAG GTGGCTCCCC ACAGTTGGGA GACCACAGGC CCCCTCTTCT
1851  GCCCCTTTTA TTTAATAAAA AAATAAAATA AAAAAAAAAA AAAAAAAAA
1901  AAAAAAAAAA AAAAAAAAAA AAAAAAAAAA AAAA
```

DR-0  AGGTCA AGGTCA

DR-1  AGGTCA c AGGTCA

DR-2  AGGTCA cc AGGTCA

DR-3  AGGTCA ctc AGGTCA

DR-4  AGGTCA ctcg AGGTCA

DR-5  AGGTCA ctcgt AGGTCA

DR-6  AGGTCA ctcgtt AGGTCA

OR-1, AN ORPHAN RECEPTOR BELONGING TO THE NUCLEAR RECEPTOR FAMILY

BACKGROUND OF THE INVENTION

1. Field of the Invention

This invention relates to cellular nuclear receptors.

2. Brief Description of the Art

A large family of nuclear receptors has been identified which confer cells with responsiveness to molecules such as retinoic acid, vitamin D3, steroid hormones and thyroid hormones. Extensive studies have shown that the members of this superfamily of nuclear receptors activate and/or repress gene transcription through direct binding to discrete cis-acting elements termed "hormone response elements" (HRE). It has been shown that these HRE's comprise repeats of consensus palindromic hexanucleotide DNA motifs. The specificity of the HRE's is determined by the orientation of, and spacing between, halfsites (i.e. half a palindromic sequence)(Umenesono K., et al, 1991 Cell 65, 1255–1266).

Specific DNA binding is mediated by a distinct DNA binding domain, containing two zinc fingers, which is conserved among all thus discovered nuclear receptors. Three amino acids at the C-terminal base of the first zinc finger (known as the "P-box") are important for the recognition of the half site nucleotide sequence. Members of the nuclear receptor superfamily have been classified into different groups on the basis of the amino acid sequence within the P box.

Molecules thought to be nuclear receptors, as they are structurally related to characterized receptors, but for which no ligand has been identified are termed "orphan receptors". Many such orphan receptors have been identified (see for example Evans R. M, (1988) Science 240,889–895 and O'Malley, B. (1990) Mol. Endocrinol. 4 363–369).

BRIEF SUMMARY OF THE INVENTION

According to one aspect of the invention there is provided a novel nuclear receptor, hereinafter termed "OR-1", having the amino acid sequence of FIG. 1 (SEQ ID NO:2) or substantially the same amino acid sequence as the amino acid sequence shown in FIG. 1 (SEQ ID NO:2) or an amino acid sequence functionally similar to that sequence.

Figure 1:
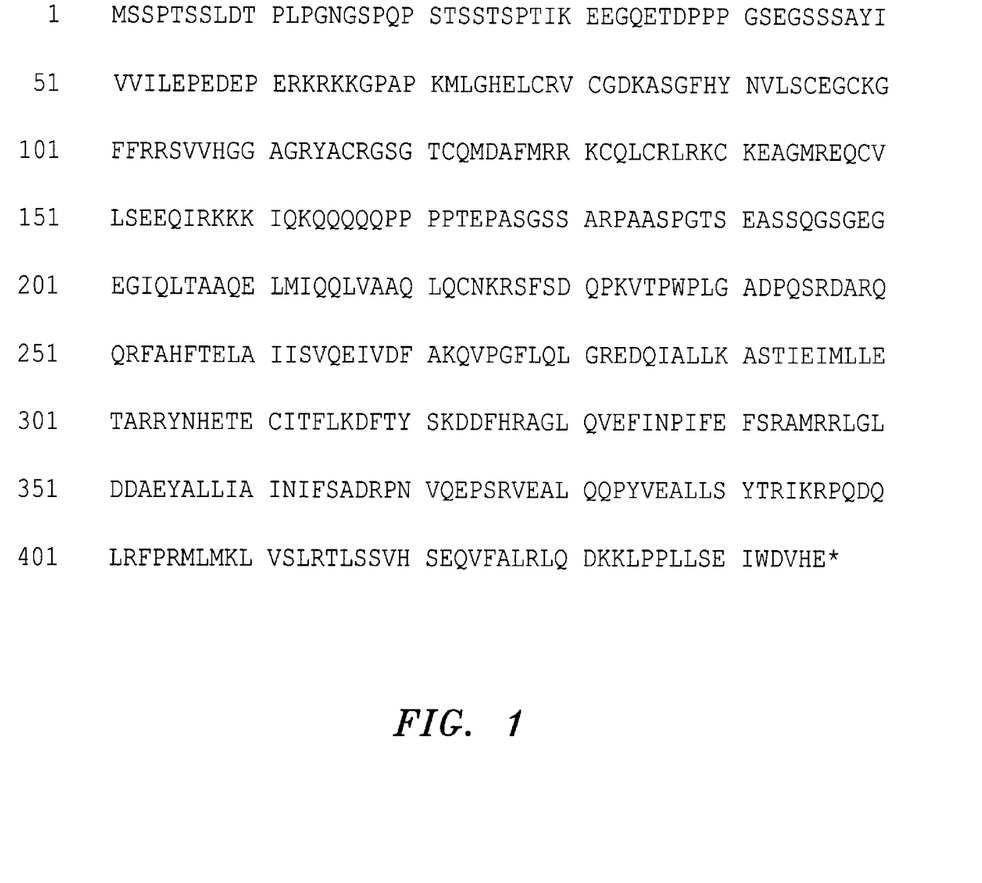
FIG. 1 shows the amino acid sequence of a nuclear receptor of the invention (SEQ ID NO:2)

An amino acid sequence which is more than about 90%, preferably more than 95%, identical with the sequence shown in FIG. 1 (SEQ ID NO:2) is substantially the same amino acid sequence for the purposes of the present application.

Figure 2A:
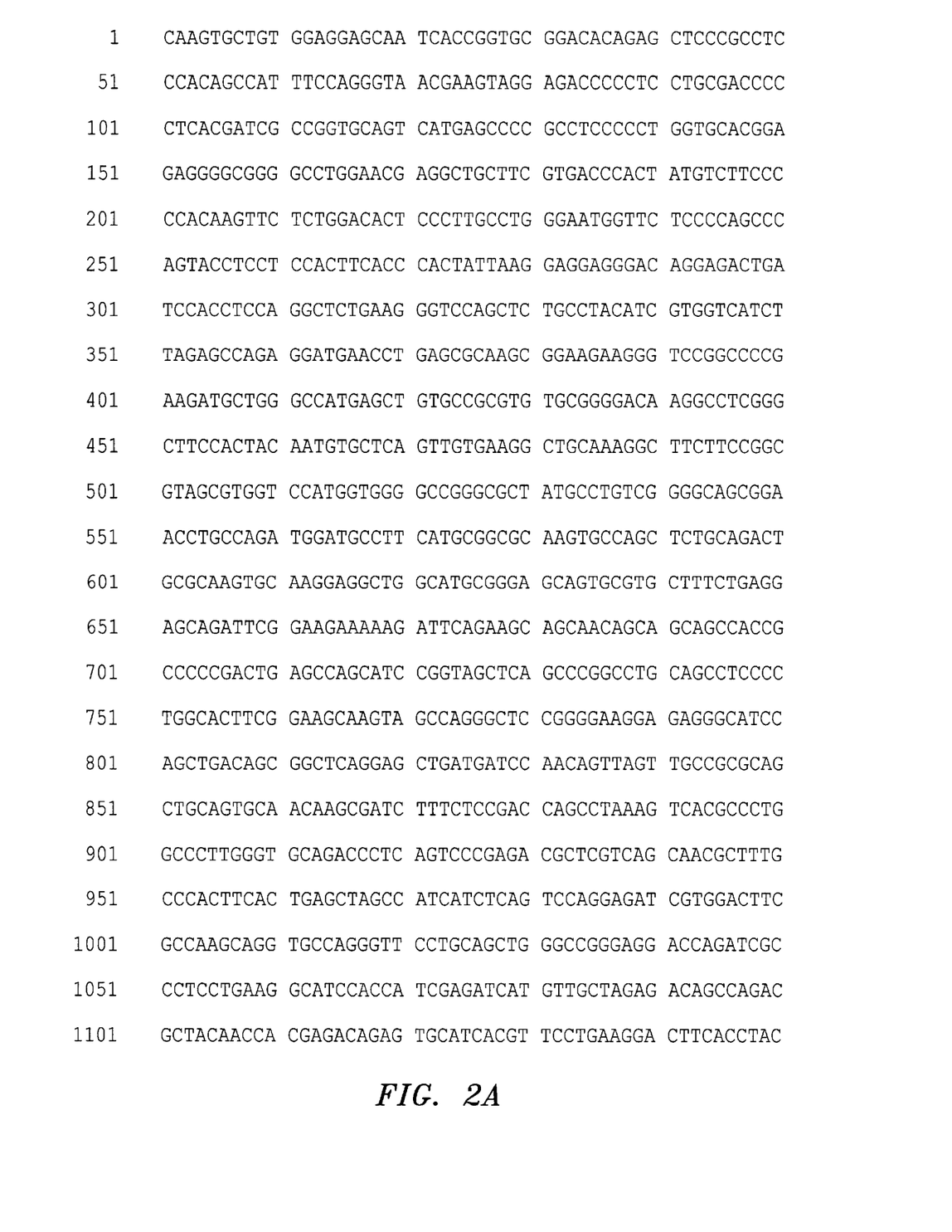
FIGS. 2A and 2B show the DNA sequence of a nuclear receptor of the invention (SEQ ID NO:1)
Figure 2B:
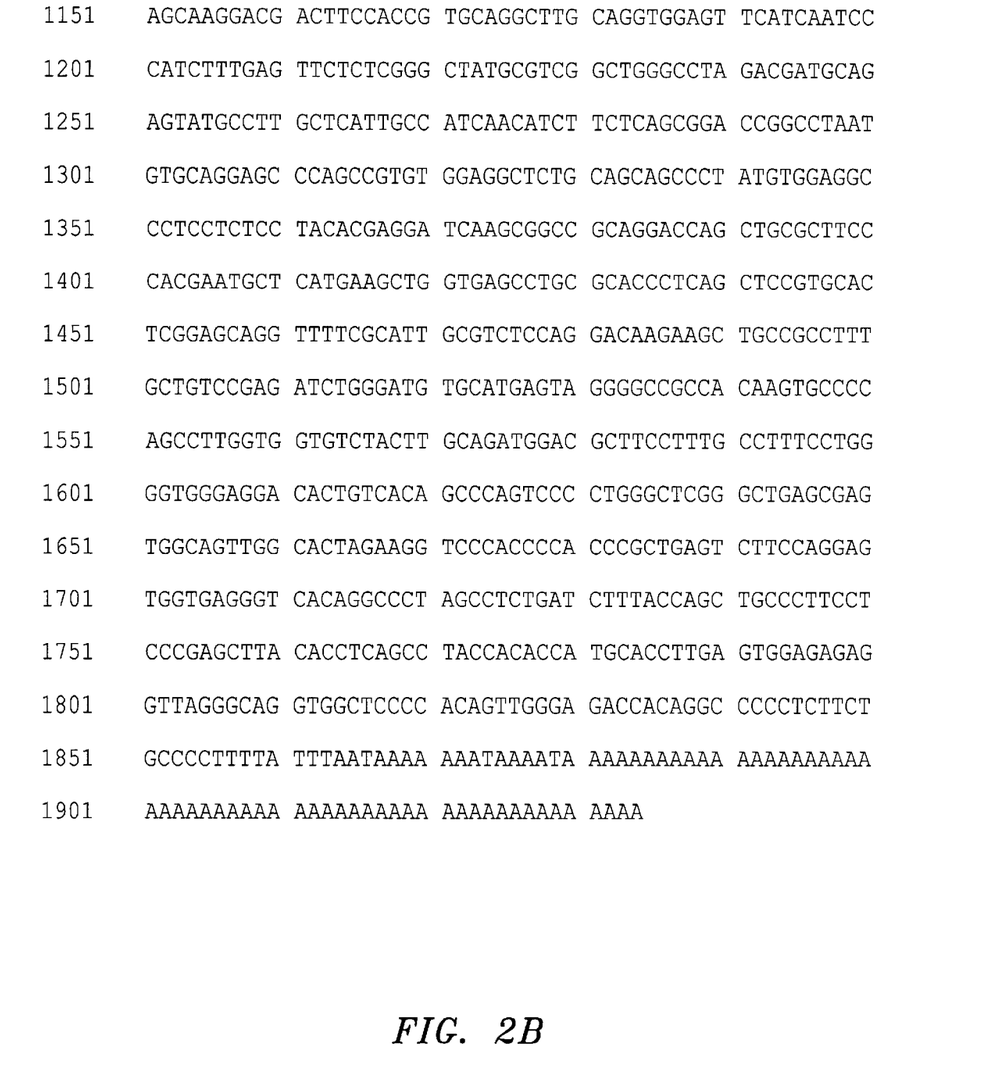

According to another aspect of the invention there is provided a DNA sequence encoding a nuclear receptor according to the first aspect of the invention. Preferably, the DNA sequence is that given in FIG. 2 (SEQ ID NO:1) or is a DNA sequence encoding a protein or polypeptide having the functionality of OR-1.

The nuclear receptor of the invention has a similar P-box configuration to the retinoic acid receptor (RAR), the vitamin D receptor (VDR), and the thyroid hormone receptor (TR) and can be placed in the same subfamily as those receptors.

Preferably, the receptor heterodimerizes with RXR to form a complex.

Preferably, the receptor interacts with RXR and binds to a DNA sequence comprising at least one repeat of the DNA sequence -AGGTCA- (SEQ ID NO:10). Preferably the sequence is AGTCAGGTCACTCGAGGTCAGTCA (SEQ ID NO:11).

Preferably, the receptor modulates 9-cis retinoic acid signalling.

BRIEF DESCRIPTION OF THE DRAWINGS

The nuclear receptor of the invention, OR-1, and its method of production will now be described, by way of example only, with reference to the accompanying drawings FIGS. 1–5, in which.

DETAILED DESCRIPTION OF THE INVENTION

Cloning and Expression of OR-1

Rat OR-1 was cloned from a cDNA library from Sprague Dawley rat liver in the commercially-available λZAP vector (Stratagene, USA) using the techniques described in G öttlicher, M. et al (1992) Proc. Natl. Acad. Sci. USA 89, 4653–4657. Foetal and adult rat tissues were excised after decapitation and frozen on dry ice. Cryostat sections were hybridized to 48-mer oligonucleotides complementary to OR-1 mRNA positions 100–151 and 850–900 as described in Dagerlind, Å et al (1992) Histochemistry 98 34–49.

Several unrelated oligonucleotides were also used as controls. The addition of 100 fold of the respective nonlabelled control oligonucleotide abolished all labelling observed with the OR-1 probes.

Plasmids

OR-1 cDNA was subcloned as an Eco RI fragment in pGEM-3Z (Promega) to produce the plasmid pROR-1-Sp6, or in the multiple cloning site of pCMV5 (described in Andersson, S. et al 1989 J. Biol. Chem., 264, 8222–8229) to produce the plasmid pCMV-OR-1. The reporter construct pDR4-AF contains a SphI-XhoI fragment of the cDNA for a secreted form of human PAP (placental alkaline phosphatase) described in (Berger, J. et al. 1988 Gene 66,1–10) under the control of a DR4-TK-containing promoter, pRRXR-T7 and pCMV-RXR described previously in Gearing, K. L. et al 1993 Proc. Natl. Acad. Sci. USA 90, 1440–1444.

DNA Binding Studies

Gel shifts were performed using in vitro-translated OR-1 and RXR with the commercially-available TNT™-coupled reticulocyte lysate system (Promega, Madison USA). Proteins were incubated on ice for 15 min with 4 μg of poly (dI-dC) and with unlabelled competitor DNA where indicated in a solution comprising 100 mM KCl; 10 mM Hepes, pH 7.6; 1 mM dithiothreitol; 1 mM EDTA; 10% (wt./vol) glycerol, before addition of 0.5 ng of a $^{32}$P-end labelled oligonucleotide probe. The reaction mixtures were incubated for a further 10 min at 22° C. before electrophoresis at 200V and 4° C. in pre-run 4% polyacryliamide/0.25 TBE (0.089 m tris-borate pH 8.3, 0.025 EDTA) gels.
The following oligonucleotides and their complements were used as probes:
DR0 AGCTTCAGGTCAAGGTCAGGTTCA (SEQ ID NO:3)
DR1 AGCTTCAGGTCACAGGTCAGTTCA (SEQ ID NO:4)
DR2 AGCTTAGGTCACCAGGTCAGTTCA (SEQ ID NO:5)
DR3 AGTCCAGGTCACTCAGGTCAGTCA (SEQ ID NO:6)
DR4 AGTCAGGTCACTCGAGGTCAGTCA (SEQ ID NO:7)
DR5 AGTCAGGTCACTCGTAGGTCAGTCA (SEQ ID NO:8)
DR6 AGTCAGGTCACTCGTTAGGTCAGTCA (SEQ ID NO:9)

Cells and Transfection

Embryonal carcinoma P19 EC cells were cultured in Dulbecco's modified Eagle's medium supplemented with 10% foetal calf serum, nonessential amino acids, penicillin (100 units/ml) and streptomycin (100 mg/ml). Chinese Hamster Ovary (CHO) cells were cultured in Ham's F-12 medium supplemented with 10% foetal calf serum, penicillin (100 units/ml) and streptomycin (100 mg/ml). Cells were plated in duplicate in 35 mm Petri dishes and transfected at 30% confluency, using lipofectin reagent (Bethesada Research Laboratories, USA) according to the recommendations of the supplier. After 12 hours the medium was changed and supplemented or not supplemented as the case may be with 100 nM 9-cis retinoic acid (a gift of Hoffman-LaRoche) as indicated, and incubated for an additional 36 h. Cell culture supernatants were then heated to 65° C. for 30 min. PAP activity was determined as the increase in $A_{405}$ at 30° C. in a 1 ml reaction mixture containing 0.75 ml of supernatant, 200 nM Tris (pH 8.8.), 275 mM NaCl, 0.5 mM $MgCl_2$, and 5 mM p-nitrophenylphosphate. Transfections were repeated 6 times with different plasmid preparations and data from a representative experiment is presented here.

Results

Figure 3:
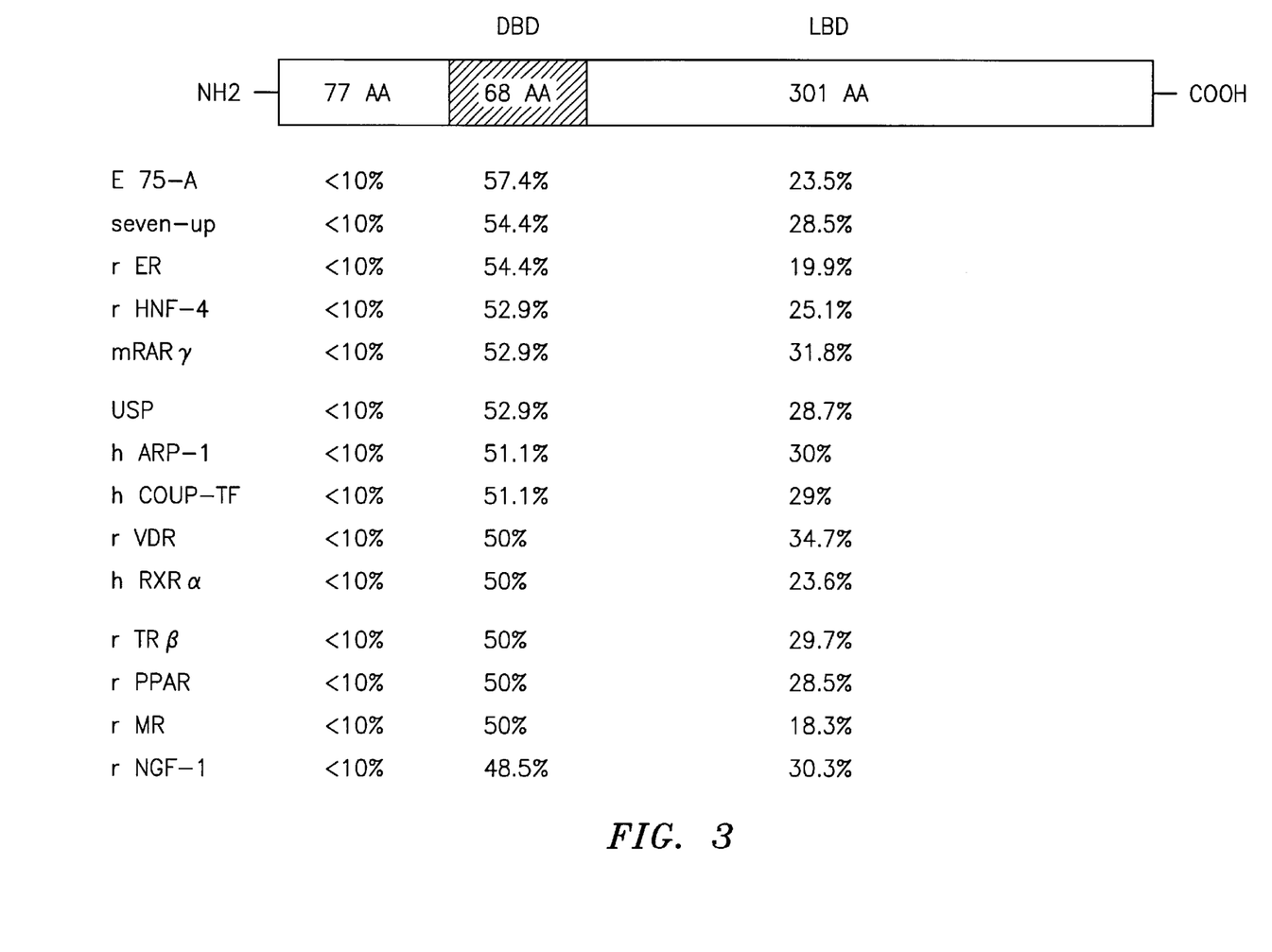
FIG. 3 gives a comparison between the primary amino acid sequences of the nuclear receptor of the invention and those of other members of the nuclear receptor superfamily.

The OR-1 clone spans 1940 bp including a 55 bp long poly-A tail and contains an open reading frame starting with an ATG corresponding to a protein of 446 amino acids with a predicted molecular weight of 50 kD. The complete amino acid and nucleotide sequences of OR-1 are given in FIGS. 1 and 2A and 2B (SEQ ID NO:2 and SEQ ID NO:1) respectively. OR-1 shows no striking homology to known members of the nuclear receptors superfamily: the highest homologies represent less than 10% in the N-terminal domain, about 50% in the DNA binding domain, and between 20–30% in the putative ligand binding domain as shown in FIG. 3. The amino-terminal domain of OR-1 (underlined in FIG. 1 (SEQ ID NO:2)) is 77 amino acids long and to a large extent comprises a so-called "PEST" sequence, meaning that it is an amino acid sequence rich in proline, glutamic acid, serine, threonine, and aspartic acid residues. The DNA binding domain consists of 68 amino acids including the nine invariable cysteines characteristic of the members of the nuclear receptor superfamily, as well as other amino acids that are found to be conserved in all members of this protein family.

Genomic Cloning

A rat genomic fragment has been isolated, that spans the DNA binding domain or OR1 and all the exons downstream of it. Most nuclear receptors for which the genomic structure has been determined have the two zinc "fingers" of the DNA binding domain encoded on separate exons. We have shown that the whole DNA-binding domain is encoded by one exon in OR1. We have furthermore shown that this is also the case with RLD-1 (*Mol. Endocrinol.* infra), a closely related receptor "knock-out" mice of OR1 and RLD-1.

Tissue Distribution of OR-1

Figure 4:
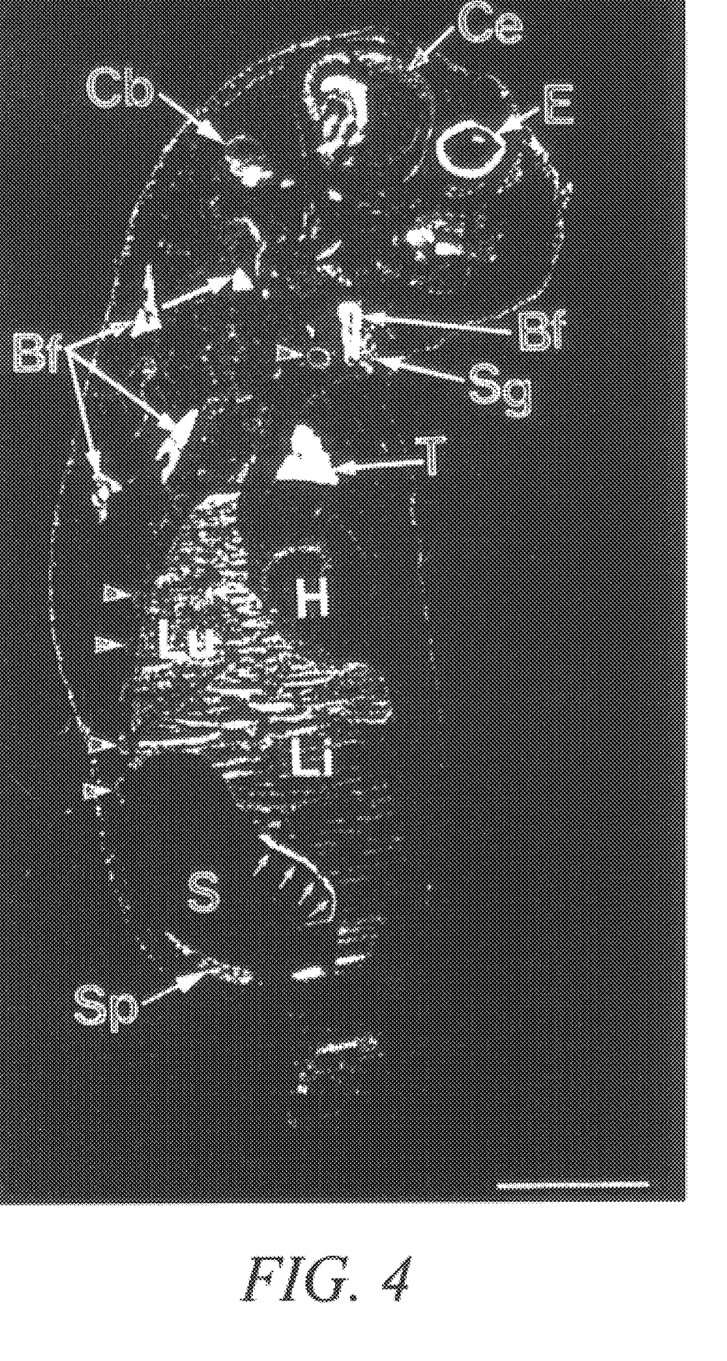
FIG. 4 Localization of OR-1 mRNA—producing cells in rat tissues with in situ hybridization.

To analyse the tissue distribution of OR-1 transcripts, in situ hybridizations were performed on foetal and adult rat tissues. Labelling for OR-1 was found in several tissues of both foetal and adult rats. As discussed, below, prominent expression was observed in liver, lung, thymus, brown fat, salivary gland, thyroid gland, pituitary gland and retina whereas moderate levels were seen in developing cerebrum and cerebellum, in perichondrium around developing bones, heart and skin. Low levels of OR-1 mRNA was present in skeletal muscle as shown in FIG. 4. In adult rats, strong labelling was found in lymph node, prostate, adrenal cortex and the intermediate lobe of the pituitary gland. Moderate levels were seen in liver, testis, salivary gland, thyroid and parathyroid gland, adrenal medulla, anterior pituitary and kidney. In the brain, a moderate signal was observed in neurons in the granular cell layer of the cerebellum and hippocampus.

1) Immune System

Prominent expression of OR-1 mRNA was seen in the cortex of the thymus with lower levels in the medulla. In dipped sections grains were seen over most of the thymocytes in the cortex. Significant expression was also seen in the lymph nodes, whereas low levels were observed in spleen. Some cells in the bone marrow expressed OR-1 mRNA.

2) Endocrine System

Significant expression of OR-1 was seen in the anterior and intermediate lobes of the pituitary. In dipped sections grains could be seen over most of the cells in the intermediate lobe and over the majority of the cells in the anterior lobe. The posterior lobe appeared virtually nonlabelled. Prominent expression of OR-1 was detected in the parathyroid glands where most of the cells expressed OR-1 mRNA. In the thyroid gland moderate expression was observed and OR-1 mRNA was heterogenously distributed in different cell types. Most of the parafollicular cells expressed OR-1, whereas only part of the follicular cells were labelled. High expression in the adrenal gland was observed in all layers of the cortex, whereas lower levels were seen in the medulla. Expression of OR-1 was slightly higher in the zona glomerulosa than in the rest of the cortex. In the adrenal medulla the labelling was heterogenous and part of the chromaffin cells and ganglion cells expressed OR-1. In pineal gland some cells contained OR-1 mRNA.

3) Reproductive System

OR-1 could be detected both in male and female genital organs. In the testis OR-1 mRNA was present in all cross-sections of the seminiferous tubules. The labelling localizes to the basal compartment of the seminiferous epithelium and grains could be seen mainly over primary spermatocytes, whereas spermatogonia and germ cells at later developmental stages were non-labelled. The Sertoli cells and Leydig cells did not express OR-1 mRNA. A strong signal for OR-1 was evident in the epithelium of the prostate gland and also in the epididymis, whereas low levels were seen in the epithelium of the vesicula seminalis. In the ovary oocytes at different stages of development expressed OR-1 mRNA while other cells appeared non-labelled. In the uterus the epithelium was strongly labelled and lower levels of OR-1 mRNA were seen in the myometrium.

4) Urinary System

Moderate expression of OR-1 could be detected in the outer medulla of the kidney, whereas in the cortex and inner medulla the labelling was very low or nondetectable. In dipped sections grains were seen over different parts of the loop of Henle. The glomeruli, proximal and distal convoluted tubules and collecting tubules did not express OR-1 at detectable levels. The transitional epithelium of the renal pelvis expressed OR-1.

5) Digestive System

In salivary glands the secretory acini and the ducts expressed moderate levels of OR-1 mRNA. In the liver OR-1 mRNA was evenly distributed throughout the liver and most, if not all, hepatocytes were labelled. In the intestinal tract OR-1 was expressed in the epithelium of stomach and small and large intestine.

6) Nervous System

Significant expression of OR-1 was seen in the sympathetic and sensory ganglia. In superior cervical ganglion most of the sympatetic neurons expressed OR-1 at high level and also the satellite cells were labelled. In dorsal root ganglion the labelling was heterogenous and varied between individual neurons. The Schwan cells of peripheral nerves expressed OR-1 whereas oligodendrocytes in optic nerve were nonlabelled. In the retina the bipolar cells expressed OR-1. In the central nervous system OR-1 mRNA was seen in several areas including hippocampus and cerebellum.

7) Respiratory System

Moderate expression of OR-1 was seen in the bronchial epithelium and in the alveoli.

8) Other Tissues

Low or non-detectable levels of OR-1 were seen in sketal muscle and heart. Also in white adipose tissue OR-1 expression was below the detection limit. In skin a clear signal was observed in keratinocytes in the basal part of the epidermis. A strong signal was seen in perichondrium around the cartilage in trachea. Low expression of OR-1 could be seen in intra and extraorbital lacrimal glands.

The expression of OR-1 thus appears to be ubiquitous, suggesting that this receptor might have a house keeping function and/or mediate many effects by regulating the transcriptor of various genes. The tissue distribution or OR-1 is different from the tissue distribution of RLD-1 (*Mol Endocrinol* 9, 72–85, 1995) suggesting that these two isoforms might have different functions. OR-1 is particularly well expressed in tissues involved in the immue system. It has been described that 9-cis retinoic acid plays a role in thymocyte development, being a potent negative regulator of activation-induced T-cell apoptosis. Since OR-1 dimerizes with RXR and is expressed at a high level in the thymus during the fetal stages, it may play a role in regulating T-cells development. OR-1 is also well expressed in peripheral endocrine glands, in male and female genital organs and in the nervous system. The tissue distribution of OR-1 is thus different from that of RXRα which has been described to be noticeably abundant in visceral tissues such as liver, kidney, lung, brain, heart, intestine and testis. We previously suggested that OR-1 could act as a helper of RXRα in mediating the effects of 9-cis retinoic acid. Nevertheless we do not know whether OR-1 could also act as a monomer, as a homodimer or as a heterodimer with another protein than RXRα. For example, it is possible that OR-1 modulates the actions of RXRβ that shows a diffuse and probably ubiouitous expression, and of RXRγ which has a more specific distribution.

OR-1 Interacts with RXR on a DR4 Motif in Vitro

A set of potential HRE's, DR0–DR6, having the DNA sequences described above predicted by the 3-4-5 rule (Umensono et al supra) was synthesized and assayed in gel shift experiments using in vitro translated OR-1 alone or in combination with RXR also translated in vitro. In vitro translation of OR-1 produced a protein of the predicted size of 50 kD. In the gel shift assays, OR-1 was unable to bind to any of the potential HRE's but OR-1 combined with RXR, recognized the potential HRE DR4 which is usually described as the thyroid hormone response element (TRE) (Umensono et al supra).

Figure 5A:
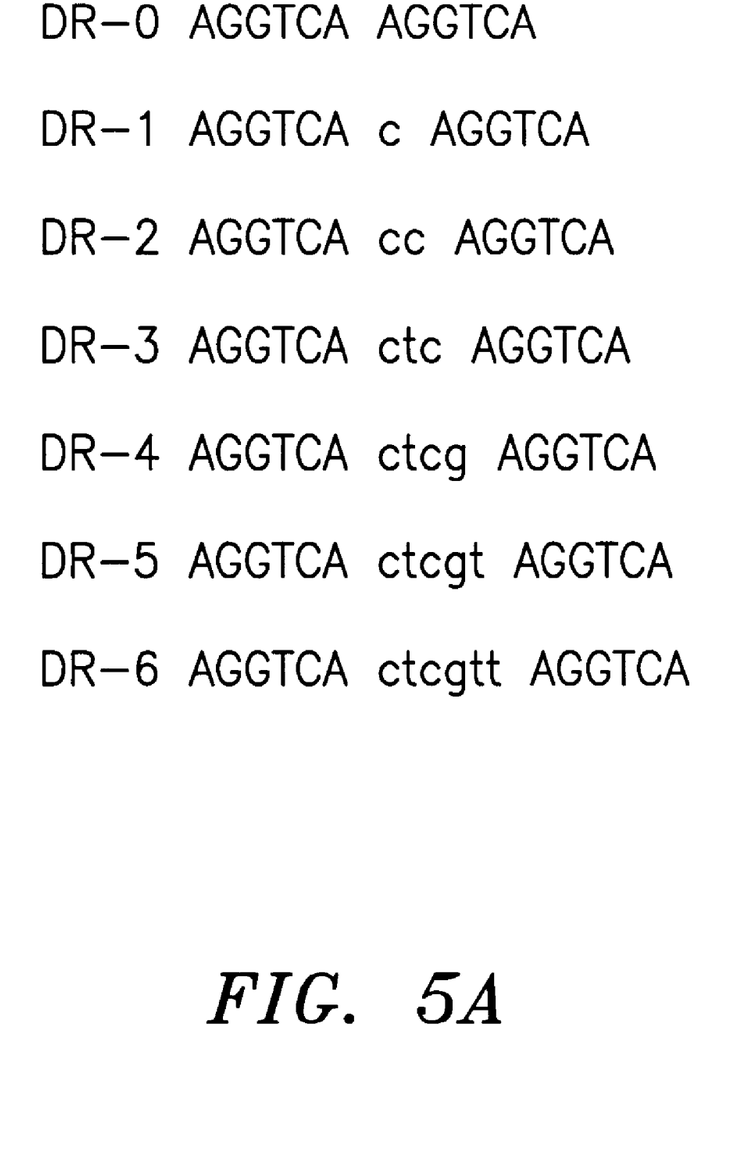
FIG. 5A gives the DNA sequences of seven potential HRE's DR-0–DR-6.
Figure 5B:
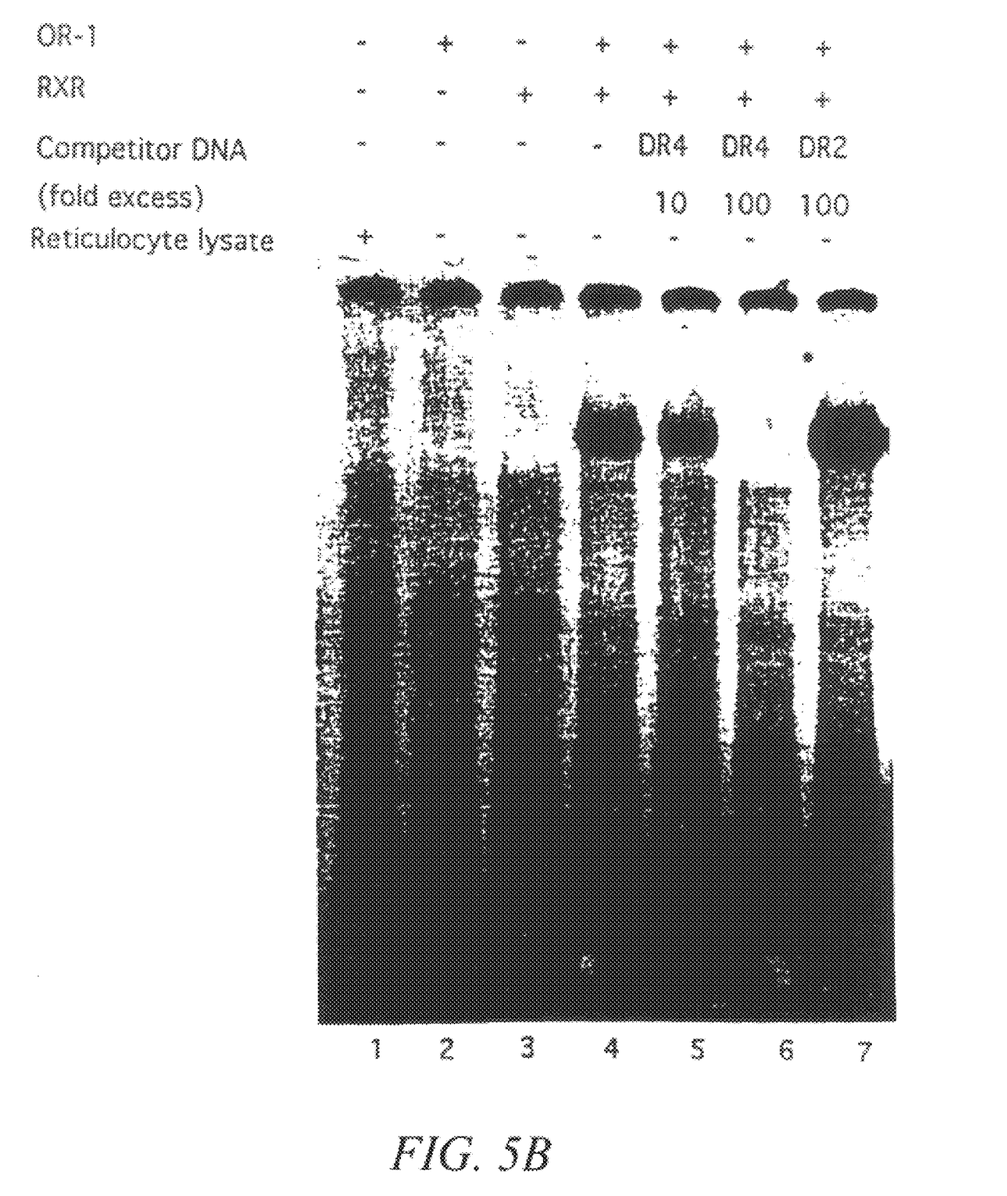
FIG. 5B illustrates the interaction between OR-1 or the retinoid X receptor (RXR) and the potential HRE's, DR-2 and DR4.
Figure 6:
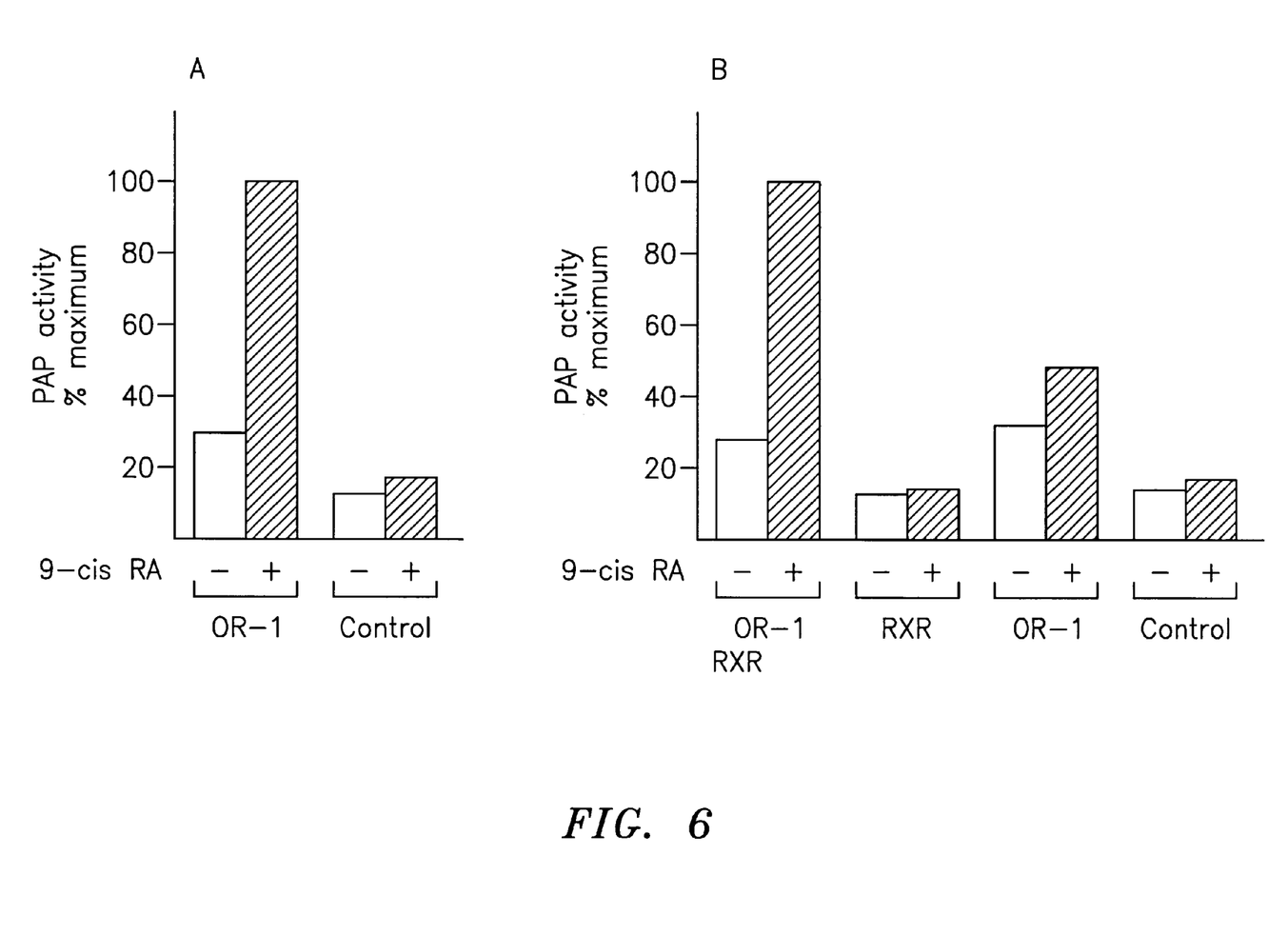
FIG. 6 illustrates experiments showing that OR-1 confers 9-cis retinoic acid-responsiveness of RXR on a DR4-containing promoter.

FIG. 5B shows that although OR-1 or RXR alone was not able to bind to DR4, together these proteins were able to form a specific complex with this DNA element. The appearance of this complex depends on the presence of RXR and is inhibited by a 10-fold excess of the specific DNA target element, but not by a 100-fold excess of an unrelated DNA element—see FIG. 5B, lane 7)

OR-1 Confers 9-Cis Retinoic Acid Responsiveness or RXR on a DR4-Containing Promoter Since OR-1 and RXR formed a specific complex on the DR4 sequence in vitro, coexpression of OR-1 in embryonal carcinoma (EC) cells that express endogenous RXR was tested to determine whether it could affect the activity of a reporter gene under the control of a DR4-containing promoter. RXR has been shown to be an auxiliary receptor for several classes of hormone receptors, controlling the ligand responses of receptors that form heterodimers with RXR (Yu, V. C. et al 1991 *Cell* 67, 251–1266 and Bugge, T. H. et al 1992 *EMBO J.* 11, 1409–1418). In addition, it has been shown that 9-cis retinoic acid leads to effective RXR homodimer formation and that these homodimers bind and activate several retinoic acid response elements ("RARE's"), but not natural thyroid hormone response elements (Zhang, X. K. et al 1992 *Nature* (London)358, 587–591). As previously described by others (Hallenbeck, P. L. et al 1993, *J. Biol Chem.*268, 3825–3828) our transfection studies showed no induction by 9-cis retinoic acid of RXR on a reporter containing DR4 (FIG. 5). Expression of OR-1 allowed activation of RXR by 9-cis retinoic acid on a DR4-containing promoter. In CHO cells that do not express endogenous RXR at as high a level as EC cells, cotransfection of RXR together with OR-1 is necessary to obtain induction by 9-cis retinoic acid. Thus acting as a helper of RXR, OR-1 appears to confer 9-cis retinoic acid signalling on DR4-containing promoters.

What is claimed is:

1. An isolated nuclear receptor, comprising a polypeptide consisting of the amino acid sequence of SEQ ID NO:2.

2. A complex comprising the receptor of claim 1 and RXR.

3. An isolated nuclear receptor, comprising a polypeptide consisting of the amino acid sequence of SEQ ID NO:2, wherein said receptor binds to a DNA sequence comprising at least one repeat of the sequence AGGTCA (SEQ ID NO:10).

4. An isolated nuclear receptor, comprising a polypeptide consisting of the amino acid sequence of SEQ ID NO:2, wherein said receptor binds to a DNA sequence comprising the sequence AGTCAGGTCACTCGAGGTCAGTCA (SEQ ID NO:11).

5. An isolated polypeptide consisting of the amino acid sequence of SEQ ID NO:2.

6. An isolated nucleic acid which codes for a polypeptide consisting of the amino acid sequence of SEQ ID NO:2.

7. The isolated nucleic acid of claim 6, wherein said isolated nucleic acid consists of the nucleic acid sequence of SEQ ID NO:1.

* * * * *

UNITED STATES PATENT AND TRADEMARK OFFICE
CERTIFICATE OF CORRECTION

PATENT NO. : 6,277,976 B1
DATED : August 21, 2001
INVENTOR(S) : Eva Enmark et al.

It is certified that error appears in the above-identified patent and that said Letters Patent is hereby corrected as shown below:

<u>Column 16,</u>
Lines 15-20, cancel claims 6 and 7.

Signed and Sealed this

Thirteenth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO.   : 6,277,976 B1
DATED        : August 21, 2001
INVENTOR(S)  : Eva Enmark et al.

It is certified that error appears in the above-identified patent and that said Letters Patent is hereby corrected as shown below:

<u>Column 16,</u>
Lines 15-19, cancel claims 6 and 7.

Signed and Sealed this

Fifteenth Day of June, 2004

JON W. DUDAS
*Acting Director of the United States Patent and Trademark Office*

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
       (A) LENGTH: 1934 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO:1:

```
CAAGTGCTGT GGAGGAGCAA TCACCGGTGC GGACACAGAG CTCCCGCCTC CCACAGCCAT      60

TTCCAGGGTA ACGAAGTAGG AGACCCCCTC CTGCGACCCC CTCACGATCG CCGGTGCAGT     120

CATGAGCCCC GCCTCCCCCT GGTGCACGGA GAGGGCGGG  GCCTGGAACG AGGCTGCTTC     180

GTGACCCACT ATGTCTTCCC CCACAAGTTC TCTGGACACT CCCTTGCCTG GAATGGTTC      240

TCCCCAGCCC AGTACCTCCT CCACTTCACC CACTATTAAG GAGGAGGGAC AGGAGACTGA     300

TCCACCTCCA GGCTCTGAAG GGTCCAGCTC TGCCTACATC GTGGTCATCT TAGAGCCAGA    360

GGATGAACCT GAGCGCAAGC GGAAGAAGGG TCCGGCCCCG AAGATGCTGG GCCATGAGCT    420

GTGCCGCGTG TGCGGGGACA AGGCCTCGGG CTTCCACTAC AATGTGCTCA GTTGTGAAGG    480

CTGCAAAGGC TTCTTCCGGC GTAGCGTGGT CCATGGTGGG GCCGGGCGCT ATGCCTGTCG    540

GGGCAGCGGA ACCTGCCAGA TGGATGCCTT CATGCGGCGC AAGTGCCAGC TCTGCAGACT    600

GCGCAAGTGC AAGGAGGCTG GCATGCGGGA GCAGTGCGTG CTTTCTGAGG AGCAGATTCG    660

GAAGAAAAAG ATTCAGAAGC AGCAACAGCA GCAGCCACCG CCCCCGACTG AGCCAGCATC    720

CGGTAGCTCA GCCCGGCCTG CAGCCTCCCC TGGCACTTCG GAAGCAAGTA GCCAGGGCTC    780

CGGGGAAGGA GAGGGCATCC AGCTGACAGC GGCTCAGGAG CTGATGATCC AACAGTTAGT    840

TGCCGCGCAG CTGCAGTGCA ACAAGCGATC TTTCTCCGAC CAGCCTAAAG TCACGCCCTG    900

GCCCTTGGGT GCAGACCCTC AGTCCCGAGA CGCTCGTCAG CAACGCTTTG CCCACTTCAC    960

TGAGCTAGCC ATCATCTCAG TCCAGGAGAT CGTGGACTTC GCCAAGCAGG TGCCAGGGTT   1020

CCTGCAGCTG GGCCGGGAGG ACCAGATCGC CCTCCTGAAG GCATCCACCA TCGAGATCAT   1080

GTTGCTAGAG ACAGCCAGAC GCTACAACCA CGAGACAGAG TGCATCACGT TCCTGAAGGA   1140

CTTCACCTAC AGCAAGGACG ACTTCCACCG TGCAGGCTTG CAGGTGGAGT TCATCAATCC   1200

CATCTTTGAG TTCTCTCGGG CTATGCGTCG GCTGGGCCTA GACGATGCAG AGTATGCCTT   1260

GCTCATTGCC ATCAACATCT TCTCAGCGGA CCGGCCTAAT GTGCAGGAGC CCAGCCGTGT   1320

GGAGGCTCTG CAGCAGCCCT ATGTGGAGGC CCTCCTCTCC TACACGAGGA TCAAGCGGCC   1380

GCAGGACCAG CTGCGCTTCC CACGAATGCT CATGAAGCTG GTGAGCCTGC GCACCCTCAG   1440

CTCCGTGCAC TCGGAGCAGG TTTTCGCATT GCGTCTCCAG GACAAGAAGC TGCCGCCTTT   1500

GCTGTCCGAG ATCTGGGATG TGCATGAGTA GGGGCCGCCA CAAGTGCCCC AGCCTTGGTG   1560

GTGTCTACTT GCAGATGGAC GCTTCCTTTG CCTTTCCTGG GGTGGGAGGA CACTGTCACA   1620

GCCCAGTCCC CTGGGCTCGG GCTGAGCGAG TGGCAGTTGG CACTAGAAGG TCCCACCCCA   1680

CCCGCTGAGT CTTCCAGGAG TGGTGAGGGT CACAGGCCCT AGCCTCTGAT CTTTACCAGC   1740

TGCCCTTCCT CCCGAGCTTA CACCTCAGCC TACCACACCA TGCACCTTGA GTGGAGAGAG   1800
```

-continued

```
GTTAGGGCAG GTGGCTCCCC ACAGTTGGGA GACCACAGGC CCCCTCTTCT GCCCCTTTTA    1860

TTTAATAAAA AAATAAAATA AAAAAAAAAA AAAAAAAAAA AAAAAAAAAA AAAAAAAAAA    1920

AAAAAAAAAA AAAA                                                       1934
```

(2) INFORMATION FOR SEQ ID NO:2:

(i) SEQUENCE CHARACTERISTICS:
        (A) LENGTH: 446 amino acids
        (B) TYPE: amino acid
        (C) STRANDEDNESS: single
        (D) TOPOLOGY: linear     (ii) MOLECULE TYPE: protein     (xi) SEQUENCE DESCRIPTION: SEQ ID NO:2:

```
Met Ser Ser Pro Thr Ser Ser Leu Asp Thr Pro Leu Pro Gly Asn Gly
 1               5                  10                  15

Ser Pro Gln Pro Ser Thr Ser Ser Thr Ser Pro Thr Ile Lys Glu Glu
            20                  25                  30

Gly Gln Glu Thr Asp Pro Pro Gly Ser Glu Gly Ser Ser Ser Ser Ala
        35                  40                  45

Tyr Ile Val Val Ile Leu Glu Pro Glu Asp Glu Pro Glu Arg Lys Arg
 50                  55                  60

Lys Lys Gly Pro Ala Pro Lys Met Leu Gly His Glu Leu Cys Arg Val
65                  70                  75                  80

Cys Gly Asp Lys Ala Ser Gly Phe His Tyr Asn Val Leu Ser Cys Glu
                85                  90                  95

Gly Cys Lys Gly Phe Phe Arg Arg Ser Val His Gly Gly Ala Gly
            100                 105                 110

Arg Tyr Ala Cys Arg Gly Ser Gly Thr Cys Gln Met Asp Ala Phe Met
        115                 120                 125

Arg Arg Lys Cys Gln Leu Cys Arg Leu Arg Lys Cys Lys Glu Ala Gly
    130                 135                 140

Met Arg Glu Gln Cys Val Leu Ser Glu Glu Gln Ile Arg Lys Lys Lys
145                 150                 155                 160

Ile Gln Lys Gln Gln Gln Gln Pro Pro Pro Thr Glu Pro Ala
                165                 170                 175

Ser Gly Ser Ser Ala Arg Pro Ala Ala Ser Pro Gly Thr Ser Glu Ala
            180                 185                 190

Ser Ser Gln Gly Ser Gly Glu Gly Glu Gly Ile Gln Leu Thr Ala Ala
        195                 200                 205

Gln Glu Leu Met Ile Gln Gln Leu Val Ala Ala Gln Leu Gln Cys Asn
    210                 215                 220

Lys Arg Ser Phe Ser Asp Gln Pro Lys Val Thr Pro Trp Pro Leu Gly
225                 230                 235                 240

Ala Asp Pro Gln Ser Arg Asp Ala Arg Gln Gln Arg Phe Ala His Phe
                245                 250                 255

Thr Glu Leu Ala Ile Ile Ser Val Gln Glu Ile Val Asp Phe Ala Lys
            260                 265                 270

Gln Val Pro Gly Phe Leu Gln Leu Gly Arg Glu Asp Gln Ile Ala Leu
        275                 280                 285

Leu Lys Ala Ser Thr Ile Glu Ile Met Leu Leu Glu Thr Ala Arg Arg
    290                 295                 300

Tyr Asn His Glu Thr Glu Cys Ile Thr Phe Leu Lys Asp Phe Thr Tyr
305                 310                 315                 320
```

```
Ser Lys Asp Asp Phe His Arg Ala Gly Leu Gln Val Glu Phe Ile Asn
            325                 330                 335

Pro Ile Phe Glu Phe Ser Arg Ala Met Arg Arg Leu Gly Leu Asp Asp
            340                 345                 350

Ala Glu Tyr Ala Leu Leu Ile Ala Ile Asn Ile Phe Ser Ala Asp Arg
            355                 360                 365

Pro Asn Val Gln Glu Pro Ser Arg Val Glu Ala Leu Gln Gln Pro Tyr
            370                 375                 380

Val Glu Ala Leu Leu Ser Tyr Thr Arg Ile Lys Arg Pro Gln Asp Gln
385                 390                 395                 400

Leu Arg Phe Pro Arg Met Leu Met Lys Leu Val Ser Leu Arg Thr Leu
            405                 410                 415

Ser Ser Val His Ser Glu Gln Val Phe Ala Leu Arg Leu Gln Asp Lys
            420                 425                 430

Lys Leu Pro Pro Leu Leu Ser Glu Ile Trp Asp Val His Glu
            435                 440                 445

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

AGCTTCAGGT CAAGGTCAGG TTCA                                          24

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

AGCTTCAGGT CACAGGTCAG TTCA                                          24

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

AGCTTAGGTC ACCAGGTCAG TTCA                                          24

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO:6:

AGTCCAGGTC ACTCAGGTCA GTCA                                                  24

(2) INFORMATION FOR SEQ ID NO:7:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:7:

AGTCAGGTCA CTCGAGGTCA GTCA                                                  24

(2) INFORMATION FOR SEQ ID NO:8:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA to scRNA (xi) SEQUENCE DESCRIPTION: SEQ ID NO:8:

AGTCAGGTCA CTCGTAGGTC AGTCA                                                 25

(2) INFORMATION FOR SEQ ID NO:9:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:9:

AGTCAGGTCA CTCGTTAGGT CAGTCA                                                26

(2) INFORMATION FOR SEQ ID NO:10:

(i) SEQUENCE CHARACTERISTICS:
            (A) LENGTH: 6 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:10:

AGGTCA                                                                       6

(2) INFORMATION FOR SEQ ID NO:11:

(i) SEQUENCE CHARACTERISTICS:
            (A) LENGTH: 24 base pairs
            (B) TYPE: nucleic acid
            (C) STRANDEDNESS: double
            (D) TOPOLOGY: linear -continued (ii) MOLECULE TYPE: cDNA (xi) SEQUENCE DESCRIPTION: SEQ ID NO:11:

AGTCAGGTCA CTCGAGGTCA GTCA 24